United States Patent [19]

Johnson et al.

[11] Patent Number: 5,057,642

[45] Date of Patent: Oct. 15, 1991

[54] REMOVAL OF BASIC IMPURITIES FROM OLEFIN STREAMS

[75] Inventors: Marvin M. Johnson; Gerhard P. Nowack, both of Bartlesville, Okla.; Mary E. Rezac, Austin, Tex.

[73] Assignee: Phillips Petroleum Company, Bartlesville, Okla.

[21] Appl. No.: 687,343

[22] Filed: Apr. 18, 1991

[51] Int. Cl.$^5$ ............................................. C07C 7/12
[52] U.S. Cl. ................................. 585/823; 585/820; 423/237
[58] Field of Search ................. 585/823, 820; 423/237

[56] References Cited

U.S. PATENT DOCUMENTS

| | | | |
|---|---|---|---|
| 4,024,026 | 5/1977 | Gewartoski | 585/823 |
| 4,256,728 | 3/1981 | Nishino et al. | 422/4 |
| 4,291,920 | 9/1981 | Lingane et al. | 299/4 |
| 4,351,980 | 9/1982 | Reusser et al. | 585/820 |

Primary Examiner—Anthony McFarlane
Assistant Examiner—Nhat Phan
Attorney, Agent, or Firm—K. K. Brandes

[57] ABSTRACT

Basic impurities, in particular ammonia, are removed from monoolefin-containing feeds, in particular an isobutylene-containing feed, by contacting with a hydrated acidic clay.

17 Claims, No Drawings

REMOVAL OF BASIC IMPURITIES FROM OLEFIN STREAMS

BACKGROUND OF THE INVENTION

This invention relates to a process for removing ammonia and/or amine impurities from olefin-containing fluids. In one particular aspect, this invention relates to the removal of ammonia from a feed which contains $C_4$ monoolefins by means of a sorbent material.

The presence of ammonia or amine impurities in an olefin-containing stream for etherization processes, in particular an isobutene-containing feed stream for a methyl tertiary-butyl (MTBE) process, is detrimental because ammonia and other basic compounds deactivate acidic etherization catalysts, in particular sulfonic acid containing poly(styrene-divinylbenzene) ion-exchange resins. Generally, the monoolefin containing feed stream is "scrubbed" with a suitable acidic solution for the removal of ammonia or gaseous amine impurities. However, the installation and operation of such gas-liquid absorption processes is expensive, and it is desirable to replace them with processes employing guard beds containing solid sorbent materials. In this invention, an effective solid sorbent material removes ammonia and/or amine impurities from a monoolefin-containing stream without losing appreciable amounts of monoolefins by absorption or undesirable reactions (such as oligomerization).

SUMMARY OF THE INVENTION

It is an object of this invention to provide a process for removing ammonia and/or amine impurities from monoolefin-containing fluids. It is a particular object of this invention to remove ammonia and/or amine impurities from a fluid stream which contains $C_4$ monoolefin(s). It is a further object of this invention to treat a monoolefin-containing feed with a solid sorbent so as to remove ammonia and/or amine(s) from the feed. Further objects and advantages will become apparent from the detailed disclosure and the appended claims.

In accordance with this invention, a process for at least partially removing at least one basic impurity selected from the group consisting of ammonia, alkyl amines, cycloalkyl amines and aryl amines from a feed which comprises at least one monoolefin comprises the step of contacting said feed with a hydrated acidic clay sorbent, under such contacting conditions as to obtain a product in which the concentration of said at least one basic impurity is lower than in said feed and in which the concentration of said at least one monoolefin is essentially the same as in said feed. Preferably, the hydrated acidic clay sorbent contains about 0.05 to about 0.4 lb. of water per lb. dry clay. In one preferred embodiment, the at least one monoolefin contains 4 carbon atoms per molecule, and more preferably is isobutylene. In a particular embodiment, the at least one basic impurity is ammonia.

DETAILED DESCRIPTION OF THE INVENTION

Any suitable monoolefin-containing feed which contains basic impurities can be utilized in the process of this invention. Generally, the feed contains one or two or more than two monoolefins containing 2-5 carbon atoms per molecule. Particularly suited are butenes, i.e., 1-butene, 2-butene and isobutene (isobutylene), the latter being most preferred. The feed generally contains the monoolefin(s) at a volume percentage of about 50 to about 99.9%, preferably about 65 to about 95%. Saturated hydrocarbons, such as methane, alkane, propane, butane, isobutane, and the like may also be present in the feed and will not interfere with the process of this invention. Diolefins and acetylenes are preferably substantially absent from the feed because they may interfere with the process of this invention. The feed can be liquid or gaseous at the contacting conditions of this invention. A particularly preferred feed is one which is used as feedstock for a MTBE process (i.e., a process for reacting isobutylene with methanol so as to produce methyl t-butyl ether, used as motor fuel additive).

Non-limiting examples of basic impurities contained in the feed are ammonia, (a particularly common impurity), monoalkyl amines, dialkyl amines trialkyl amines, where the alkyl group generally contains 1-10 carbon atoms per molecule, cyclopentyl amines, cyclohexyl amines, aniline, toluidines and the like. The concentration of $NH_3$ and/or amine(s) in the feed generally is in the range of from about 1 ppm (parts by weight per million parts by weight of feed) to about 500 ppm, preferably about 5-100 ppm $NH_3$ and/or amine(s). Small amounts of water and of sulfur and oxygen-containing impurities may also be present in the feed, as long as they do not interfere with the process of this invention.

The solid materials useful as sorbent materials in this invention can be described as hydrated acid-treated smectite clays, such as montmorillonite, bentonite, vermiculite, hectorite, saponite, beidillite and the like. In these clays, approximately every sixth aluminum ion has been replaced by a magnesium ion. This produces a crystal lattice with a negative charge which is neutralized by the absorption of metallic cations (such as $Na^+$) on the surface. These surface cations are readily removed by treatment with an acid (such as HCl or $H_2SO_4$), wherein hydrogen ions are exchanged for the metallic ions. The acid-treated material can be designated a magnesium-substituted hydrogen montmorillonite. Sorbent materials of this type are sold commercially under the trade name of "Filtrol" by the Chemical Catalysts Group of Engelhard Corporation, Edison, N.J. Specific acid-treated commercial clays include Filtrol Grade 71, Filtrol Grade F24 and Filtrol Grade 25.

It is important for the intended result of the process of this invention to use an acid-treated clay which contains about 0.05 to about 0.4, preferably about 0.13-0.20, lb. water per lb. dry clay, wherein dry clay is defined as acid-treated clay which has been heated at 240° F. for 24 hours at 0 psig (i.e., at atmospheric pressure). If a commerical clay material does not contain a sufficient amount of water, the clay can be mixed with a suitable amount of water so as to provide hydrated acid-treated clay particles. An unhydrated acid-treated clay is not suitable as a sorbent for monoolefin-containing feeds because it can absorb monoolefins (as has been described in U.S. Pat. No. 4,351,980) or catalyze monoolefin dimerization and other undesirable reactions when contacted with the feed. Such monoolefin absorption and/or conversion is to be avoided because of undesirable losses of monoolefin feed material and undesirable deactivation of the sorbent material with regard to $NH_3$ and/or amine sorption. The concentration of the monoolefin(s) should be essentially the same in the product and in the feed.

A typical hydrated acid-treated clay generally has an acidity of about 5–400 mg KOH per gram sample at phenolphthalein end point, an average particle size of about 10–20 mesh, a surface area (BET/$N_2$ method) of about 200–500 $m^2$/g, and a bulk density of about 0.7–0.9 g/cc. A typical chemical formula and a mineral analysis (on a water-free basis) of a preferred clay are disclosed in column 3 of U.S. Pat. No. 4,351,980.

Any suitable equipment can be used to carry out the current invention, however, a vertical tubular guard bed reactor containing the hydrated acid-treated clay sorbent is preferred. The hydrocarbon feedstock can flow through the guard bed reactor either in a down-flow or up-flow mode. The hydrocarbon-containing feed can be gaseous or liquid during the contacting with the hydrated acidic clay sorbent material.

Typical operating conditions in the guard bed are: a liquid hourly space velocity (LHSV) of the monoolefin-containing feed (if liquid at the contacting conditions) of about 0.5 to about 10 volume feed/volume sorbent material/hour, preferably about 2–4 volume feed/volume sorbent material/hour; or, alternatively (if the feed is gaseous at the contacting conditions) a gas hourly space velocity (GHSV) of about 100 to about 2,000 volume feed/volume sorbent material/hour, preferably about 500–1500 volume feed/volume sorbent material/hour; a contacting temperature in the range of from about 50 to about 250° F. (preferably about 70°–150° F); and a contacting pressure in the range of about 0 to about 500 psig (preferably about 100–300 psig). It is preferred that the exiting product contain no more than about 20 ppb (parts per billion by weight), preferably no more than about 10 ppb, ammonia and/or amine.

The following example is presented to further illustrate this invention and is not to be considered as unduly limiting the scope of this invention.

EXAMPLE 925 cc of Filtrol 71 clay, an acid-treated montmorillonite clay (provided by Engelhard Corporation, Chemical Catalysts Group, Edison, N.J.) was mixed with 1 liter of distilled water. The mixture was kept in a covered beaker for 4 hours so as to form hydrated clay. Thereafter, the mixture was vacuum-filtered so as to extract excess water from the hydrated clay. The hydrated clay contained 16 lb. of $H_2O$ per 100 lb. dry clay (as determined by heating the hydrated clay at 240° F. for 16 hours).

319 grams (400 cc) of this hydrated clay was placed into a vertical guard bed reactor. A gaseous isobutylene feed stream which contained about 60 ppm $NH_3$ was first bubbled through a water-containing vessel so as to saturate the feed with water vapor. Then the wet feed was passed through the clay-containing guard bed at a rate of about 1360 cc/hr (LHSV: 3.4) at room temperature. After about 280 hours on stream when ammonia breakthrough was detected, the test was discontinued and the guard bed material was weighed. The weight increase of the hydrated acidic clay was 12.59 g, which corresponded to an absorbed $NH_3$ content of 3.9 weight-% $NH_3$, based on the weight of the hydrated clay.

Reasonable variations and modifications are possible within the scope of the disclosure of this invention and the appended claims.

That which is claimed is:

1. A process for at least partially removing at least one basic impurity selected from the group consisting of ammonia, alkyl amines, cycloalkyl amines and aryl amines from a feed which comprises at least one monoolefin, comprising the step of contacting said feed with a hydrated acidic clay, under such contacting conditions as to obtain a product in which the concentration of said at least one basic impurity is lower than in said feed and the concentration of said at least one monoolefin is essentially the same as in said feed.

2. A process in accordance with claim 1, wherein said hydrated acidic clay contains about 0.05 to about 0.4 lb. of water per lb. of dry clay.

3. A process in accordance with claim 1, wherein said hydrated clay contains about 0.13 to about 0.20 lb. of water per lb. of dry clay.

4. A process in accordance with claim 1, wherein said hydrated acidic clay is a hydrated acid-treated smectite clay.

5. A process in accordance with claim 4, wherein said hydrated acid-treated clay has an acidity of about 5–400 mg KOH per gram clay at phenolphthalein end point, a particle size of about 10–20 mesh, and a BET/$N_2$ surface area of about 200–500 $m^2$/g.

6. A process in accordance with claim 1, wherein said at least one basic impurity in said feed is ammonia.

7. A process in accordance with claim 6, wherein the concentration of ammonia in said feed is about 1 ppm to about 500 ppm $NH_3$.

8. A process in accordance with claim 1, wherein said feed contains about 50 to about 99.9 volume percent of said at least one monoolefin.

9. A process in accordance with claim 1, wherein said at least one monoolefin contains 2–5 carbon atoms per molecule.

10. A process in accordance with claim 1, wherein said at least one monoolefin contains 4 carbon atoms per molecule and said at least one basic impurity in said feed is ammonia.

11. A process in accordance with claim 10, wherein said at least one monoolefin is isobutylene and the concentration of ammonia in said feed is about 1 ppm to about 500 ppm $NH_3$.

12. A process in accordance with claim 1, wherein said contacting conditions comprise a temperature of about 50°–250° F. and a pressure of about 0–500 psig.

13. A process in accordance with claim 12, wherein said contacting conditions comprise a temperature of about 70°–150° F. and a pressure of about 100–300 psig.

14. A process in accordance with claim 12, wherein said feed is liquid at said contacting conditions.

15. A process in accordance with claim 14, wherein said contacting conditions comprise a liquid hourly space velocity of about 0.5–10 volume feed per volume hydrated acidic clay per hour.

16. A process in accordance with claim 12, wherein said feed is gaseous at said contacting conditions.

17. A process in accordance with claim 16, wherein said contacting conditions comprise a gas hourly space velocity of about 100–2,000 volume feed per volume hydrated acidic clay per hour.

* * * * *